US008632592B2

(12) United States Patent
Barrall

(10) Patent No.: US 8,632,592 B2
(45) Date of Patent: Jan. 21, 2014

(54) EXPANDABLE VERTEBRAL BODY REPLACEMENT DEVICE AND METHOD

(75) Inventor: Ben Barrall, West Chester, PA (US)

(73) Assignee: DePuy Synthes Products, LLC, Raynham, MA (US)

(*) Notice: Subject to any disclaimer, the term of this patent is extended or adjusted under 35 U.S.C. 154(b) by 27 days.

(21) Appl. No.: 13/141,239

(22) PCT Filed: Dec. 4, 2009

(86) PCT No.: PCT/US2009/006378
§ 371 (c)(1),
(2), (4) Date: Sep. 8, 2011

(87) PCT Pub. No.: WO2010/074704
PCT Pub. Date: Jul. 1, 2010

(65) Prior Publication Data
US 2011/0319996 A1    Dec. 29, 2011

Related U.S. Application Data

(60) Provisional application No. 61/140,038, filed on Dec. 22, 2008.

(51) Int. Cl.
*A61F 2/44* (2006.01)
*A61B 17/88* (2006.01)

(52) U.S. Cl.
USPC ........................................ 623/17.12; 606/279

(58) Field of Classification Search
USPC ................. 623/17.11–17.16; 606/105, 279
See application file for complete search history.

(56) References Cited

U.S. PATENT DOCUMENTS

| 4,932,975 | A | | 6/1990 | Main et al. | |
|---|---|---|---|---|---|
| 5,674,294 | A | * | 10/1997 | Bainville et al. | 623/17.16 |
| 6,332,894 | B1 | * | 12/2001 | Stalcup et al. | 623/17.11 |
| 6,423,083 | B2 | * | 7/2002 | Reiley et al. | 606/192 |
| 6,733,533 | B1 | * | 5/2004 | Lozier | 623/17.12 |
| 6,958,077 | B2 | * | 10/2005 | Suddaby | 623/17.11 |
| 6,981,989 | B1 | | 1/2006 | Fleischmann et al. | |
| 6,984,246 | B2 | * | 1/2006 | Huang | 623/17.13 |
| 7,563,284 | B2 | * | 7/2009 | Coppes et al. | 623/17.12 |
| 7,799,079 | B2 | * | 9/2010 | Hestad et al. | 623/17.12 |
| 8,043,381 | B2 | * | 10/2011 | Hestad et al. | 623/17.16 |

(Continued)

FOREIGN PATENT DOCUMENTS

| DE | 20-2005-009478 | 9/2005 |
|---|---|---|
| FR | 2723841 A1 | 3/1996 |

(Continued)

*Primary Examiner* — Ellen C Hammond
*Assistant Examiner* — Jacqueline Johanas
(74) *Attorney, Agent, or Firm* — Woodcock Washburn LLP

(57) ABSTRACT

Vertebral body replacement apparatuses, systems, and methods are provided. In various examples, an implantable device is configured to be inserted between a first vertebral body and a second vertebral body. The implantable device includes a first endplate configured to contact the first vertebral body. A second endplate is configured to contact the second vertebral body. An expansion bladder is disposed between and coupled to the first endplate and the second endplate. The expansion bladder includes a first chamber and a second chamber. The first chamber and the second chamber are sealed from fluid communication with one another. An injection port is disposed through one of the first endplate or second endplate. The injection port includes a first channel in fluid communication with the first chamber and a second channel in fluid communication with the second chamber.

9 Claims, 6 Drawing Sheets

(56) References Cited

U.S. PATENT DOCUMENTS

| | | | |
|---|---|---|---|
| 8,070,813 B2* | 12/2011 | Grotz et al. | 623/17.11 |
| 8,236,057 B2* | 8/2012 | Wirtel et al. | 623/17.12 |
| 8,273,124 B2* | 9/2012 | Renganath et al. | 623/17.12 |
| 8,460,383 B2* | 6/2013 | Wirtel et al. | 623/17.12 |
| 2003/0009226 A1* | 1/2003 | Graf | 623/17.16 |
| 2005/0090901 A1* | 4/2005 | Studer | 623/17.12 |
| 2005/0119752 A1* | 6/2005 | Williams et al. | 623/17.16 |
| 2005/0197702 A1* | 9/2005 | Coppes et al. | 623/17.12 |
| 2005/0216084 A1 | 9/2005 | Fleischmann et al. | |
| 2005/0251259 A1* | 11/2005 | Suddaby | 623/17.12 |
| 2006/0149380 A1* | 7/2006 | Lotz et al. | 623/17.12 |
| 2006/0247780 A1* | 11/2006 | Bert | 623/17.16 |
| 2007/0162136 A1* | 7/2007 | O'Neil et al. | 623/17.12 |
| 2007/0168042 A1* | 7/2007 | Hudgins et al. | 623/17.16 |
| 2007/0173940 A1* | 7/2007 | Hestad et al. | 623/17.12 |
| 2007/0233254 A1* | 10/2007 | Grotz et al. | 623/17.11 |
| 2007/0288095 A1* | 12/2007 | Wirtel et al. | 623/17.16 |
| 2008/0058931 A1* | 3/2008 | White et al. | 623/17.11 |
| 2008/0132934 A1* | 6/2008 | Reiley et al. | 606/192 |
| 2008/0288073 A1* | 11/2008 | Renganath et al. | 623/17.12 |
| 2009/0222093 A1* | 9/2009 | Liu et al. | 623/17.12 |
| 2009/0270987 A1* | 10/2009 | Heinz et al. | 623/17.16 |
| 2010/0057204 A1* | 3/2010 | Kadaba et al. | 623/17.12 |
| 2010/0063510 A1* | 3/2010 | Arlet et al. | 606/93 |
| 2010/0087924 A1* | 4/2010 | Arlet | 623/17.12 |
| 2010/0145455 A1* | 6/2010 | Simpson et al. | 623/17.16 |
| 2010/0268340 A1* | 10/2010 | Capote et al. | 623/17.12 |
| 2012/0245695 A1* | 9/2012 | Simpson et al. | 623/17.16 |

FOREIGN PATENT DOCUMENTS

| | | |
|---|---|---|
| WO | WO 2007/124078 A2 | 11/2007 |
| WO | WO 2007/146896 A2 | 12/2007 |
| WO | WO 2008/011371 A2 | 1/2008 |
| WO | WO 2008/148210 A1 | 12/2008 |
| WO | WO 2010/074704 A1 | 7/2010 |

* cited by examiner

EXPANDABLE VERTEBRAL BODY REPLACEMENT DEVICE AND METHOD

CROSS-REFERENCE TO RELATED APPLICATIONS

This application is the National Stage of International Application No. PCT/US2009/006378, filed Dec. 4, 2009, which claims the benefit of U.S. Provisional Application No. 61/140,038, filed Dec. 22, 2008, the disclosures of which are incorporated herein by reference in their entireties for all purposes.

TECHNICAL FIELD

This patent document pertains generally to orthopedics. More particularly, but not by way of limitation, this patent document pertains to a system, apparatus, and method for vertebral body replacement for the spine.

BACKGROUND

Vertebral body replacement devices are indicated to provide anterior column support following a corpectomy, vertebrectomy, or spondylectomy as a result of trauma to the spine, removal of tumor material from the spinal column, or to correct spinal deformity. Surgeons typically utilize a number of different devices to provide this anterior column support, including structural bone struts made from auto- or allograft tissue, structural titanium mesh cages, expandable titanium devices, and makeshift constructs using polymethylmethacrylate (PMMA) cement and other common surgical devices, such as chest tubes, Steinmann pins, bone screws, etc., to reinforce and/or contain the cement.

In cases in which it is desirable to address the patient's pathology from a posterior or posterolateral approach, the patient's neurological structures, such as the spinal cord, cauda equina, and exiting nerve roots, limit access to the corpectomy defect, limiting the use of many of the currently available devices or forcing the surgeon to use an implant size or configuration that is less than optimal. In such cases, surgeons often opt to use PMMA to fill the defect size since it can be injected through a narrow channel and can easily conform to the individual patient's anatomy. Often, the PMMA is supplemented with another device to reinforce and/or contain the cement. However, cement constructs are difficult to revise, the PMMA allows a limited working time window, and the PMMA undergoes an exothermic curing reaction that can damage surrounding tissues. Further, there is little or no fusion potential when using these constructs and their application is typically limited to patients with a low life expectancy, e.g., tumor patients.

BRIEF DESCRIPTION OF THE DRAWINGS

In the drawings, like numerals describe similar components throughout the several views. Like numerals having different letter suffixes represent different instances of similar components. The drawings illustrate generally, by way of example, but not by way of limitation, various embodiments discussed in the present document.

DETAILED DESCRIPTION

Figure 1:
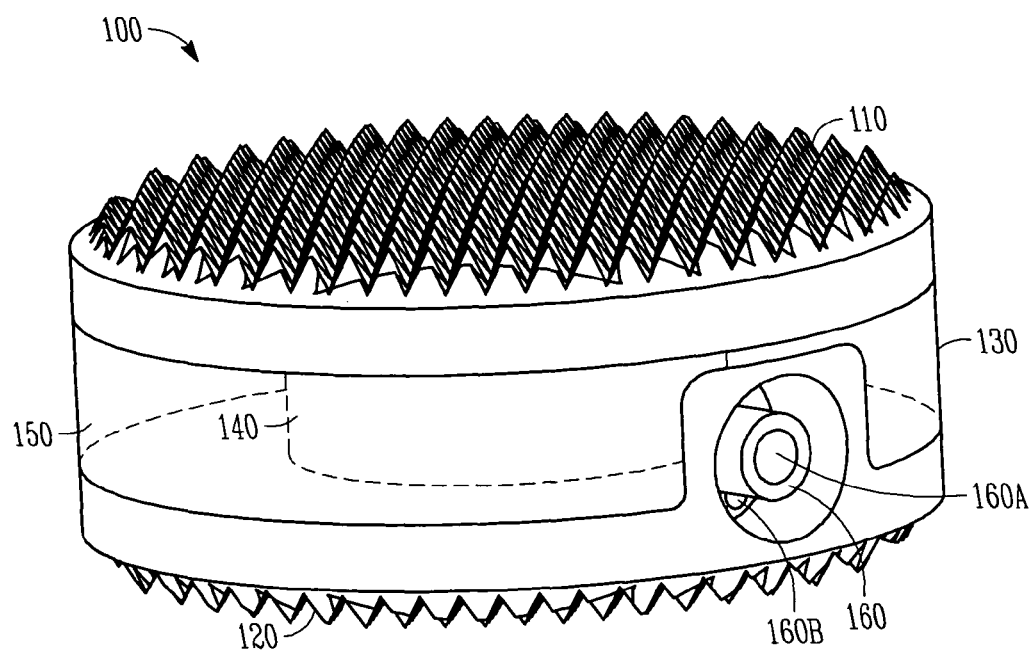
FIG. 1 illustrates a front perspective view of an expandable corpectomy implant in accordance with an example of the present invention in a collapsed configuration.

Certain terminology is used in the following description for convenience only and is not limiting. The words "right", "left", "lower", and "upper" designate directions in the drawings to which reference is made. The words "inwardly" or "distally" and "outwardly" or "proximally" refer to directions toward and away from, respectively, the geometric center of the low insertion profile vertebral body replacement implant, related instruments and related parts thereof. The words, "anterior", "posterior", "superior," "inferior" and related words and/or phrases designate preferred positions and orientations in the human body to which reference is made and are not meant to be limiting. The terminology includes the above-listed words, derivatives thereof and words of similar import.

The present inventor has recognized, among other things, that limited access to a corpectomy defect from a posterior or posterolateral approach presents problems during vertebral body replacement surgical procedures. The present inventor has further recognized that there exists an unmet need for a corpectomy implant configured for posterior or posterolateral approach that can be introduced in a minimally invasive, tissue-sparing manner, and provide stable structural support.

This patent document describes, among other things, apparatuses, systems, and methods for vertebral body replacement for the spine. In various examples, an implantable device is configured to be inserted between a first vertebral body and a second vertebral body. The implantable device includes a first endplate configured to contact the first vertebral body. A second endplate is configured to contact the second vertebral body. An expansion bladder is disposed between and coupled to the first endplate and the second endplate. The expansion bladder includes a first chamber and a second chamber. The first chamber and the second chamber are sealed from fluid communication with one another. An injection port is disposed through one of the first endplate or second endplate. The injection port includes a first channel in fluid communication with the first chamber and a second channel in fluid communication with the second chamber.

In Example 1, an implantable device is configured for insertion between a first vertebral body and a second vertebral body. The implantable device comprises a first endplate configured to contact the first vertebral body. A second endplate is configured to contact the second vertebral body. An expansion bladder is disposed between and coupled to the first endplate and the second endplate. The expansion bladder includes a first chamber and a second chamber. The first chamber and the second chamber are sealed from fluid communication with one another. An injection port is disposed through one of the first endplate or second endplate. The injection port includes a first channel in fluid communication with the first chamber and a second channel in fluid communication with the second chamber.

In Example 2, the implantable device of Example 1 optionally is configured such that the second chamber surrounds the first chamber.

In Example 3, the implantable device of one or more of Examples 1-2 optionally is configured such that the second chamber is substantially concentrically disposed around the first chamber.

In Example 4, the implantable device of one or more of Examples 1-3 optionally is configured such that the expansion bladder is configured to expand with filling of at least one of the first and second chambers with a material. Expansion of the expansion bladder causes the first and second endplates to move apart from each other.

In Example 5, the implantable device of Example 4 optionally is configured such that at least one of the first and second chambers is configured to be at least partially filled with saline.

In Example 6, the implantable device of one or more of Examples 4-5 optionally is configured such that at least one of the first and second chambers is configured to be at least partially filled with air.

In Example 7, the implantable device of one or more of Examples 4-6 optionally is configured such that at least one of the first and second chambers is configured to be at least partially filled with a structural support material.

In Example 8, the implantable device of Example 7 optionally is configured such that the structural support material includes polymethylmethacrylate.

In Example 9, the implantable device of one or more of Examples 1-8 optionally is configured such that at least one of the first and second endplates is annular.

In Example 10, the implantable device of Example 9 optionally is configured such that both of the first and second endplates are annular.

In Example 11, the implantable device of Example 10 optionally is configured such that the first chamber of the expansion bladder is disposed at open areas of the annular first and second endplates.

In Example 12, the implantable device of one or more of Examples 1-11 optionally is configured such that the expansion bladder includes two or more first chambers.

In Example 13, the implantable device of one or more of Examples 1-12 optionally is configured such that the expansion bladder includes two or more second chambers.

In Example 14, a vertebral body replacement system comprises an implantable device for insertion between a first vertebral body and a second vertebral body. The implantable device comprises a first endplate configured to contact the first vertebral body. A second endplate is configured to contact the second vertebral body. An expansion bladder is disposed between and coupled to the first endplate and the second endplate. The expansion bladder includes a first chamber and a second chamber. The first chamber and the second chamber are sealed from fluid communication with one another. An injection port is disposed through one of the first endplate or second endplate. The injection port includes a first channel in fluid communication with the first chamber and a second channel in fluid communication with the second chamber. A fill material introducer is configured to fluidly communicate with at least one of the first and second channels to at least partially fill at least one of the first and second chambers with a material.

In Example 15, the vertebral body replacement system of Example 14 optionally is configured such that the fill material introducer includes a first fill material introducer configured to fluidly communicate with the first channel to at least partially fill the first chamber with a first material and a second fill material introducer configured to fluidly communicate with the second channel to at least partially fill the second chamber with a second material.

In Example 16, the vertebral body replacement system of Example 15 optionally is configured such that the first material includes an expansion fluid and the second material includes a structural support material.

In Example 17, the vertebral body replacement system of one or more of Examples 14-16 optionally is configured such that the second chamber surrounds the first chamber.

In Example 18, the vertebral body replacement system of one or more of Examples 14-17 optionally is configured such that the second chamber is substantially concentrically disposed around the first chamber.

In Example 19, the vertebral body replacement system of one or more of Examples 14-18 optionally is configured such that the expansion bladder is configured to expand with filling of at least one of the first and second chambers with the material. Expansion of the expansion bladder causes the first and second endplates to move apart from each other.

In Example 20, a method of vertebral body replacement comprises inserting an implantable device between a first vertebral body and a second vertebral body. The implantable device includes a first endplate configured to contact the first vertebral body, a second endplate configured to contact the second vertebral body, and an expansion bladder disposed between and coupled to the first endplate and the second endplate. The expansion bladder includes a first chamber and a second chamber. The first chamber and the second chamber are sealed from fluid communication with one another. An expansion fluid is introduced into the first chamber of the expansion bladder to separate the first and second endplates of the implantable device to achieve a final height of the implantable device. A structural support material is introduced into the second chamber of the expansion bladder to maintain the final height of the implantable device.

In Example 21, the method of Example 20 optionally comprises evacuating the expansion fluid from the first chamber after introducing the structural support material into the second chamber of the expansion bladder.

In Example 22, the method of Example 21 optionally comprises introducing a substance into the first chamber after evacuation of the expansion fluid.

In Example 23, the method of Example 22 optionally is configured such that introducing the substance into the first chamber includes introducing a therapeutic substance into the first chamber.

In Example 24, the method of one or more of Examples 20-23 optionally is configured such that introducing the expansion fluid includes separating the first and second endplates of the implantable device to cause the first endplate to contact the first vertebral body and to cause the second endplate to contact the second vertebral body.

In Example 25, a method is configured for treatment of a spine including a damaged or diseased vertebral body disposed between first and second vertebral bodies. The method comprises providing an access channel to the spine. The damaged or diseased vertebral body is removed. An implantable device is inserted, through the access channel, between the first vertebral body and the second vertebral body. The implantable device includes a first endplate configured to contact the first vertebral body. A second endplate is configured to contact the second vertebral body. An expansion bladder is disposed between and coupled to the first endplate and the second endplate. The expansion bladder includes a first chamber and a second chamber. The first chamber and the second chamber are sealed from fluid communication with one another. An expansion fluid is introduced into the first chamber of the expansion bladder to separate the first and second endplates of the implantable device to achieve a final height of the implantable device. The first endplate is in contact with the first vertebral body and the second endplate is in contact with the second vertebral body. A structural support material is introduced into the second chamber of the expansion bladder to maintain the final height of the implantable device.

In Example 26, the method of Example 25 optionally comprises evacuating the expansion fluid from the first chamber after introducing the structural support material into the second chamber of the expansion bladder.

In Example 27, the method of Example 26 optionally comprises introducing a substance into the first chamber after evacuation of the expansion fluid.

In Example 28, the method of Example 27 optionally is configured such that introducing the substance into the first chamber includes introducing a therapeutic substance into the first chamber.

In Example 29, the method of one or more of Examples 25-28 optionally comprises sealing the access channel following insertion of the implantable device.

In Example 30, the method of one or more of Examples 25-29 optionally is configured such that inserting the implantable device includes inserting the implantable device with an initial height of the implantable device that is less than the final height.

Figure 2:
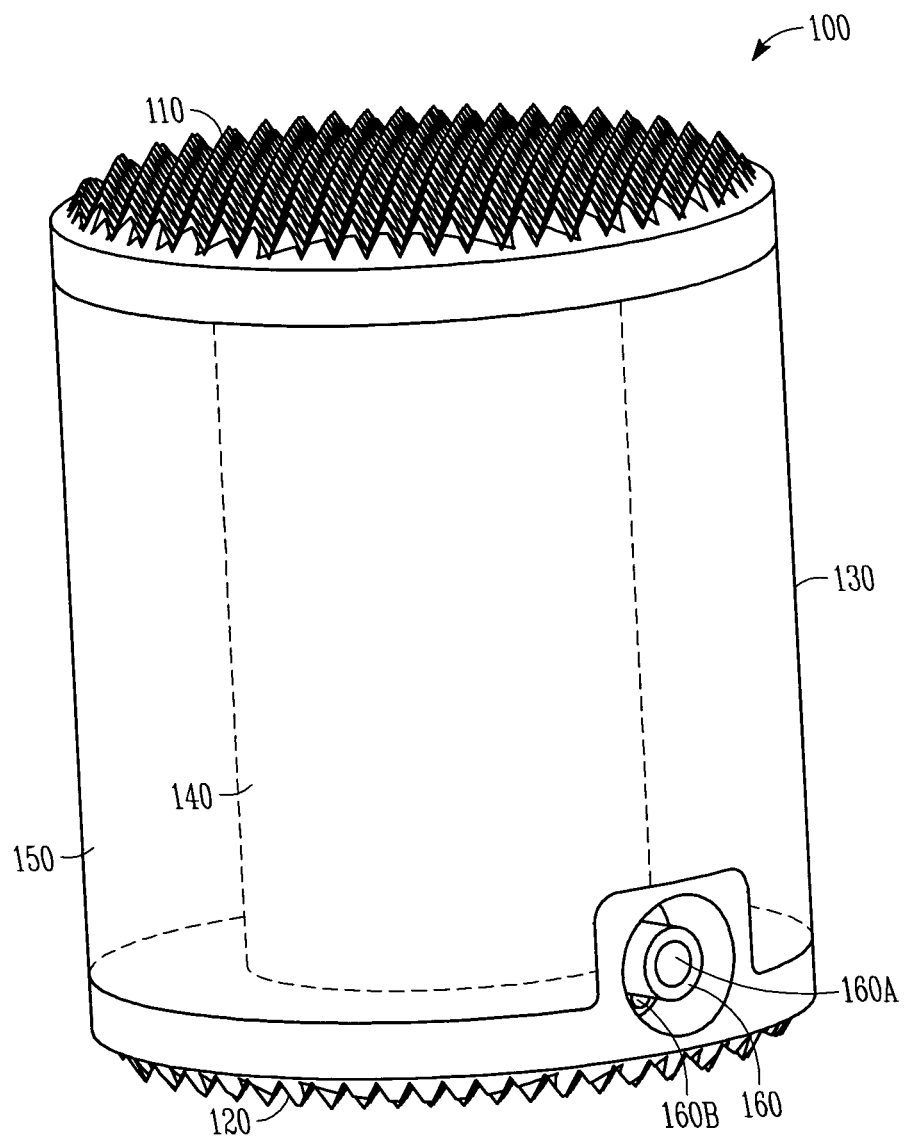
FIG. 2 illustrates a front perspective view of the expandable corpectomy implant of FIG. 1 in an expanded configuration.

Referring to FIGS. 1 and 2, in an example, an expandable corpectomy implant 100 includes a superior endplate 110 configured to contact the inferior endplate of a superior vertebral body and an inferior endplate 120 configured to contact the superior endplate of an inferior vertebral body. In various examples, the superior and inferior endplates 110, 120 include teeth, serrations, ridges, or other anti-repulsion features to secure the endplates 110, 120 to the superior and inferior vertebral bodies. In some examples, the superior and inferior endplates 110, 120 are detachable from the expandable corpectomy device 100 and can include a variety of modular geometries, including circular, ovular, kidney bean-shaped, etc., to conform to the adjacent vertebral bodies. The superior and inferior endplates 110, 120, in further examples, can be flat, tapered, concave, or convex to further accommodate the anatomy of the adjacent vertebral endplates. In a further example, the superior and inferior endplates 110, 120 can include brachytherapy seeds for treating tumors or may be coated or surface treated with beneficial agents. In still further examples, the superior and inferior endplates 110, 120 can be formed from rigid biocompatible material, such as titanium, stainless steel, or polymers such as PEEK. In another example, the superior and inferior endplates 110, 120 can be formed from conformable material to enable the superior and inferior endplates 110, 120 to conform to the anatomical shape of the adjacent vertebral endplates.

In an example, an expansion bladder 130 that, in a further example, is divided into an inner chamber 140 and an outer chamber 150 is coupled to the superior and inferior endplates 110, 120 and extends therebetween. The outer chamber 150, in an example, is concentrically disposed about the inner chamber 140. The expansion bladder 130 can be divided into the isolated inner and outer chambers 140, 150 or a pair of expansion bladders can be used to form the inner and outer chambers 140, 150. The expansion bladder 130 can be coupled to the endplates 110, 120 using a mechanical or chemical bond or a combination of both that is capable of withstanding the expansion pressures required and the normal operating conditions of the implant 100. The endplates 110, 120, in an example, include annular undercut grooves corresponding to the interface between the walls of the bladder 130 and the endplates 110, 120 such that the bladder 130 can be injection molded in a way that the walls of the bladder 130 fill into the grooves inherent on the endplates 110, 120. The expansion bladder 130 can be formed from a variety of biocompatible elastomeric or non-elastic materials such as medical grade balloon material. In an example, the expansion bladder 130 is formed from a material having an expansion bias, such that the bladder expands more readily in a first direction than in other directions. The walls of the expansion bladder 130 that form the inner chamber 140 and/or the outer chamber 150 can be reinforced with one or more annular rings or coils to provide enhanced hoop strength.

An injection port 160, in an example, is disposed through the inferior endplate 120, as shown best in FIGS. 4A, 4B, and 5A-5C, and is in fluid communication with both the inner chamber 140 and the outer chamber 150. In a further example, the injection port 160 is divided into two channels 160A, 160B for fluid introduction, a first channel 160A configured for introducing expansion medium into the outer chamber 150 and a second channel 160B for introducing expansion medium into the inner chamber 140. In another example, the injection port 160 is disposed through the superior endplate 110.

In operation and in continuing reference to FIGS. 1 and 2, in an example, an access channel is provided to the spine and a portion of a damaged or diseased vertebral body in need of replacement is removed. The implant 100, in a collapsed configuration, is coupled to an insertion instrument and implanted in the space left by the removed portion of the diseased or damaged vertebral body. Once the implant 100 is determined to be optimally positioned with respect to the vertebral bodies, a pressured fluid, such as saline, or air is temporarily injected or pumped into the outer chamber 150 by coupling a fill material introducer to the injection port 160. Introduction of the temporary pressurized fluid or air to the outer chamber 150 via the injection port 160 forces the height of the implant 100 to expand and the superior and inferior endplates 110, 120 to be distracted from one another until they bear against and impart a desired amount of distraction to the inferior endplate of the superior remaining vertebral body and the superior endplate of the inferior remaining vertebral body, thereby providing provisional anterior column support, distraction, and/or restoration of proper spinal alignment. Once the desired implant height is achieved via the filling of the outer chamber 150, in an example, a second fill material introducer is coupled to the injection port 160 and the inner chamber 140 is filled with a permanent structural support material, such as PMMA, for instance, that is capable of being introduced in a fluid state and curing to a solid state to create a permanent, structural load bearing form. Once the permanent structural support material cures within the inner chamber 140, the temporary pressurized fluid or air housed within the outer chamber 150 is evacuated and a rigid, expanded implant 100 remains. In various examples, the permanent structural support material can incorporate bone graft, brachytherapy seeds, antibiotic, radiotherapeutic, or chemotherapeutic substances. The access channel is then sealed and the wound closed.

In an example, the outer chamber 150 can be provisionally expanded and collapsed numerous times before committing to a final configuration or height for the implant 100, allowing a surgeon to optimize the size or expanded height of the implant 100 before introducing the permanent structural support material to the inner chamber 140. In a further example, the containment of the permanent structural support material within the inner chamber 140 isolates the permanent structural support material from the surrounding anatomy. In a further example, the temporary fluid contained within the outer chamber 150 can serve as a thermal insulator, protecting the nearby sensitive anatomical structures from the increased temperatures associated with any exothermic reactions that may occur during the curing of the permanent structural support material within the inner chamber 140.

In an example, the temporary expansion fluid can be introduced to the inner chamber 140 and the permanent structural support material can be introduced to the outer chamber 150. Upon curing of the permanent structural material within the outer chamber 150 and the evacuation of the temporary expansion fluid within the inner chamber 140, an empty inner chamber 140 is left that, in various examples, can be filled with bone graft, brachytherapy seeds, or antibiotic, radiotherapeutic, or chemotherapeutic substances. The implant 100 is not limited to inclusion of the inner and outer chambers 140, 150 and, in some examples, the implant 100 can include a plurality of outer chambers and/or a plurality of inner chambers.

In various examples, the walls of the inner chamber 140 and/or the outer chamber 150 can be formed from materials of varying permeability to enable various beneficial substances to leach out of the implant 100 and into the surrounding anatomy postoperatively.

In further examples, the walls of the expansion bladder 130 can feature mechanical expansion mechanism(s), such as a telescopic, accordion-like, extension spring-like, etc., mechanism, as opposed to or in addition to the elastomeric material.

In an example, the implant 100 includes two separate injection ports 160 to communicate with the inner chamber 140 and the outer chamber 150 separately. In an example, the superior and inferior endplates 110, 120 each include one injection port 160, with the injection port 160 of one of the superior and inferior endplates 110, 120 in communication with one of the inner and outer chambers 140, 150, and the injection port 160 of the other of the superior and inferior endplates 110, 120 in communication with the other of the inner and outer chambers 140, 150. In another example, one of the superior and inferior endplates 110, 120 includes two injection ports 160, with one injection port 160 in communication with the inner chamber 140, and the other injection port 160 in communication with the outer chamber 150. In a further example, both injection ports can be disposed adjacent one another on either the superior endplate 110 or the inferior endplate 120.

Figure 3:
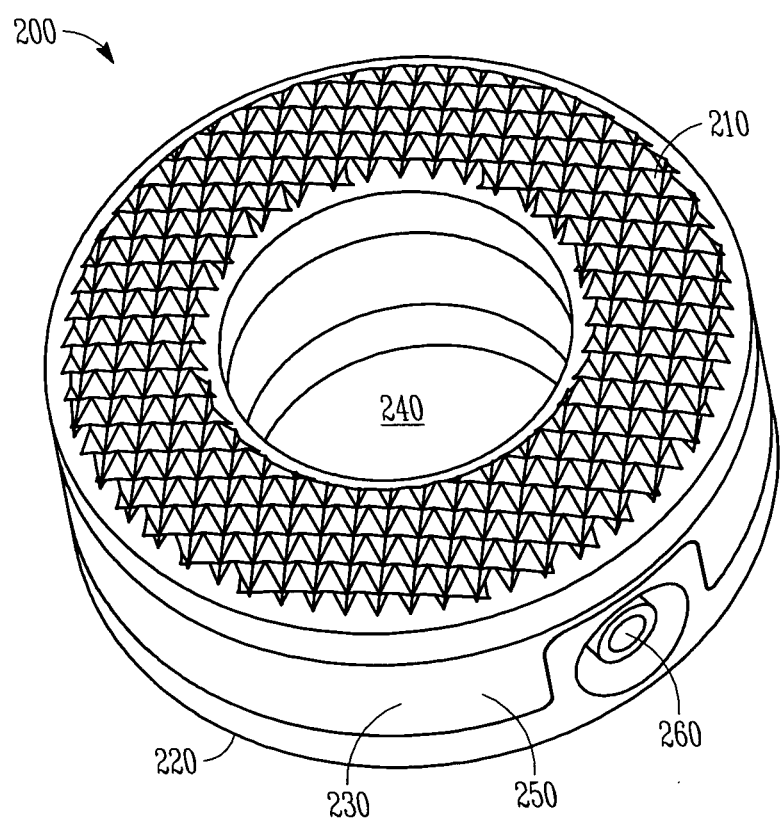
FIG. 3 illustrates a top perspective view of an expandable corpectomy implant in accordance with an example of the present invention.
Figure 4A:
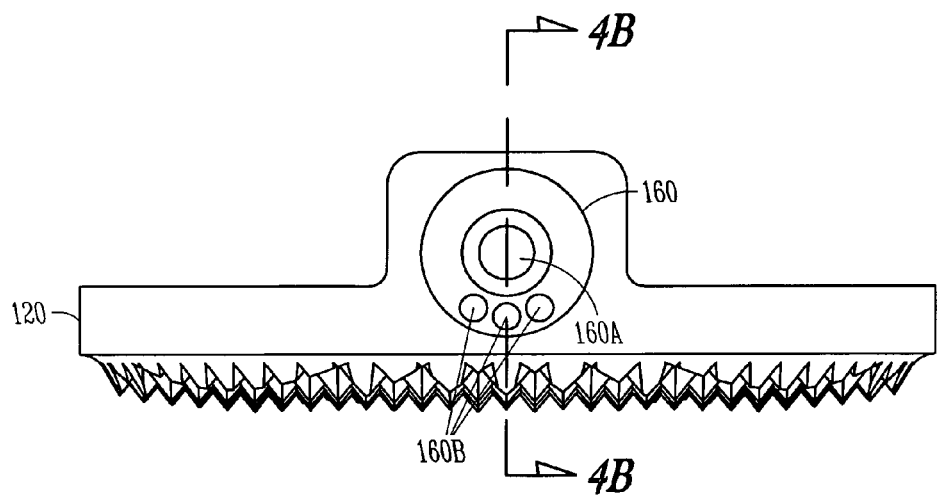
FIGS. 4A and 4B illustrate a front elevational view and a side cross-sectional view, respectively, of an inferior endplate of the expandable corpectomy implant of FIG. 1.
Figure 4B:
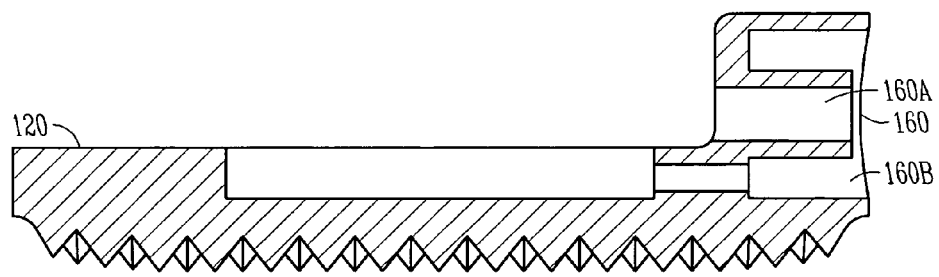
Figure 5B:
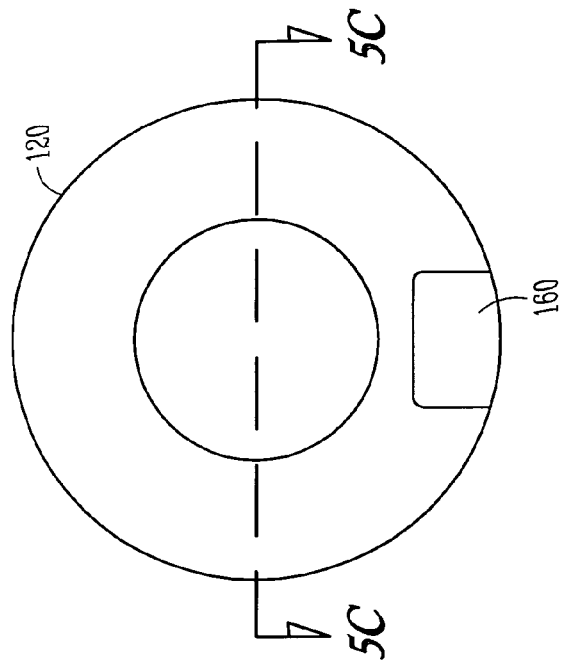
FIGS. 5A-5C illustrate a top perspective view, a bottom plan view, and a side cross-sectional view, respectively, of the inferior endplate of the expandable corpectomy implant of FIG. 1.
Figure 5C:
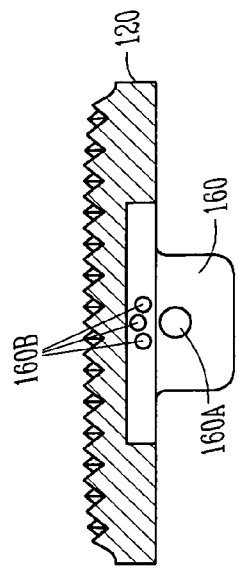
Figure 5A:
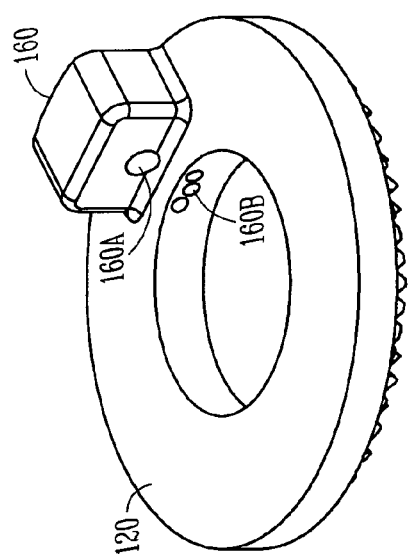

In another example, and in reference to FIG. 3, an expandable corpectomy device 200 is provided that includes an annular superior endplate 210 and an annular inferior endplate 220 that are similar in design and function to the example superior and inferior endplates 110, 120, with the exception that an axial bore 240 is provided through one or both of the superior and inferior endplates 210, 220. In an example, the expandable corpectomy device 200 includes an expansion bladder 230 that includes a single outer chamber 250. In an example, the expansion bladder 230 forms the outer chamber, which includes an annular geometry, such that the axial bore 240 is provided through the height of the implant 200. The expandable corpectomy device 200, in a further example, includes an injection port 260 that is in communication with the interior of the outer chamber 250 as well as the axial bore 240.

In operation and in continuing reference to FIG. 3, in an example, the expandable corpectomy device 200 is inserted in a collapsed configuration into the space left by the removed portion of the diseased or damaged vertebral body, as described above. Pressured fluid, such as saline or air is temporarily injected or pumped into the outer chamber 250 by coupling a fill material introducer to the injection port 260 and the superior and inferior endplates 210, 220 are distracted until a desired amount of height characterizes the implant 200. In an example, permanent structural support material is then introduced via the injection port to the axial bore 240, the permanent structural support material coming into direct contact with the inferior endplate of the superior remaining vertebral body and the superior endplate of the inferior remaining vertebral body. Upon curing of the permanent structural support material within the axial bore 240, the temporary expansion fluid is evacuated from the outer chamber 250.

In various examples, the implant 200 can include more than one outer chamber. In a further example, the inner chamber is replaced with an axial bore for permitting fusion through the assembly, such that temporary fluid can be injected into some of the outer chambers and structural support material can be injected into the remaining outer chamber(s).

In an example, two separate expansion bladders can be used to form the inner chamber 140 and the outer chamber 150. In an example, the implant 100 or the implant 200 can be modified slightly to provide an expandable interbody spacer implant.

Figure 6:
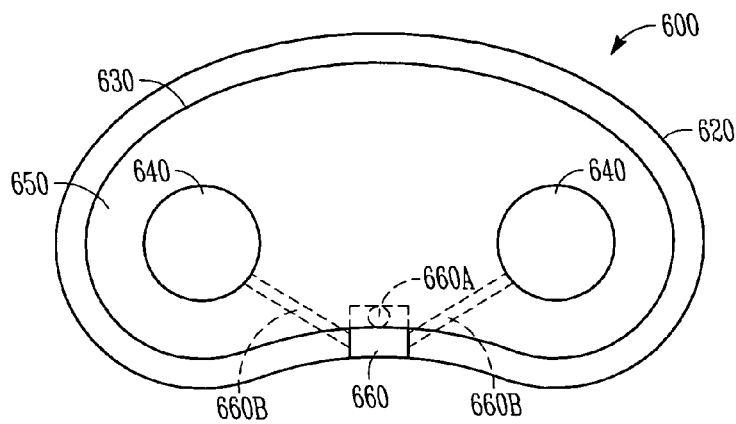
FIG. 6 illustrates a top view of an expandable corpectomy implant in accordance with an example of the present invention, the implant shown with an endplate broken away for purposes of illustration.
Figure 7:
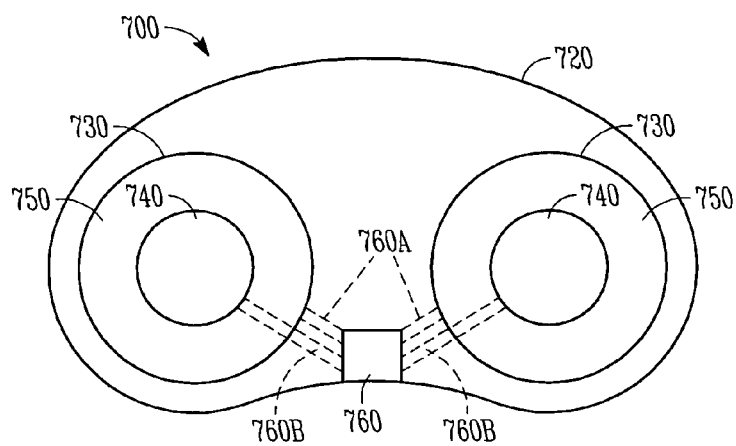
FIG. 7 illustrates a top view of an expandable corpectomy implant in accordance with an example of the present invention, the implant shown with an endplate broken away for purposes of illustration.
Figure 8:
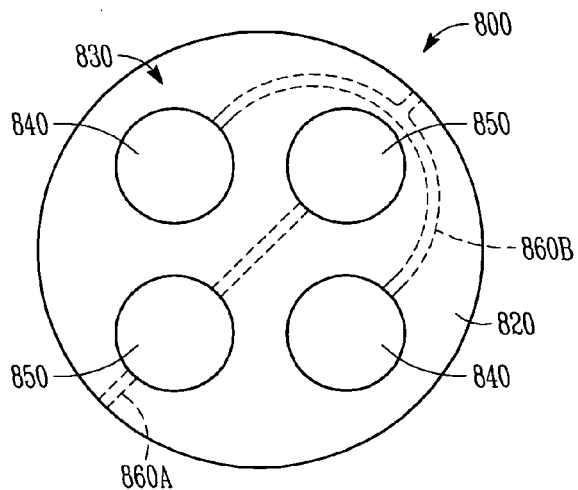
FIG. 8 illustrates a top view of an expandable corpectomy implant in accordance with an example of the present invention, the implant shown with an endplate broken away for purposes of illustration.

Referring to FIGS. 6-8, in various examples, implants can include various combinations and/or configurations of chambers. For instance, FIG. 6 shows an example of an expandable corpectomy device 600. It is noted that, in various examples, in addition to the features and properties described below, the implant 600 can include one or more features and/or one or more properties similar to those included with the implant examples discussed above. In an example, the implant 600 includes a first endplate (broken away in FIG. 6) configured to contact a first vertebral body and a second endplate 620 configured to contact a second vertebral body. In various examples, the first endplate and the second endplate 620 include teeth, serrations, ridges, or other anti-repulsion features to secure the first endplate and the second endplate 620 to the respective vertebral bodies.

In an example, the implant 600 includes an expansion bladder 630. As shown in FIG. 6, the expansion bladder 630 includes two first chambers 640 and a second chamber 650. In an example, the first chambers 640 are disposed within or otherwise surrounded by the second chamber 650. It is contemplated that, in other examples, the expansion bladder 630 of the implant 600 includes more or fewer than two first chambers and/or more than one second bladder depending upon the application of the implant 600, the patient, the insertion location of the implant 600, or other relevant factors. Although the first chambers 640 are shown as substantially circular in cross section and the second chamber 650 is shown as substantially kidney-shaped in cross section, it is noted that the first and second chambers 640, 650 can include shapes other than those that are shown in FIG. 6, again depending upon the application of the implant 600, the patient, the insertion location of the implant 600, or other relevant factors.

An injection port 660, in an example, is disposed through the second endplate 620 and is in fluid communication with both the first chambers 640 and the second chamber 650. In a further example, the injection port 660 is divided into two channels 660A, 660B for fluid introduction, with a first channel 660A configured for introducing expansion medium into the second chamber 650 and a second channel 660B for introducing expansion medium into the first chambers 640. In the example of FIG. 6, the second channel 660B branches off to each of the first chambers 640 to allow for introduction of expansion medium into each of the first chambers 640. In another example, the injection port 660 is disposed through the first endplate.

In an example, once the implant 600 is determined to be optimally positioned with respect to the vertebral bodies, a pressured fluid, such as saline, or air is temporarily injected or pumped into the second chamber 650 by coupling a fill material introducer to the injection port 660. Introduction of the temporary pressurized fluid or air to the second chamber 650 via the injection port 660 forces the height of the implant 600 to expand and the first endplate and the second endplate 620 to be distracted from one another until they bear against and impart a desired amount of distraction between the remaining vertebral bodies, thereby providing provisional anterior column support, distraction, and/or restoration of proper spinal alignment. Once the desired implant height is achieved via the filling of the second chamber 650, in an example, a second fill material introducer is coupled to the injection port 660, and the first chambers 640 are filled with a permanent structural support material, such as PMMA, for instance, that is capable of being introduced in a fluid state and curing to a solid state to create a permanent, structural load bearing form. Once the permanent structural support material cures within the first chambers 640, the temporary pressurized fluid or air housed within the second chamber 650 is evacuated and a rigid, expanded implant 600 remains. In various examples, the permanent structural support material can incorporate bone graft, brachytherapy seeds, antibiotic, radiotherapeutic, or chemotherapeutic substances. The access channel is then sealed and the wound closed. In another example, the first chambers 640 can be filled with the temporary pressurized fluid or air and the second chamber 650 can be filled with the permanent structural support material.

In another example, FIG. 7 shows an expandable corpectomy device 700. It is noted that, in various examples, in addition to the features and properties described below, the implant 700 can include one or more features and/or one or more properties similar to those included with the implant examples discussed above. In an example, the implant 700 includes a first endplate (broken away in FIG. 7) configured to contact a first vertebral body and a second endplate 720 configured to contact a second vertebral body. In various examples, the first endplate and the second endplate 720 include teeth, serrations, ridges, or other anti-repulsion features to secure the first endplate and the second endplate 720 to the respective vertebral bodies.

In an example, the implant 700 includes expansion bladders 730. As shown in FIG. 7, the implant 700 includes two expansion bladders 730, each including a first chamber 740 and a second chamber 750. In an example, each first chamber 740 is disposed within or otherwise surrounded by each second chamber 750. It is contemplated that, in other examples, the implant 700 includes more than two expansion bladders 730 depending upon the application of the implant 700, the patient, the insertion location of the implant 700, or other relevant factors. Although the first chambers 740 are shown as substantially circular in cross section and the second chambers 750 are shown as substantially annular in cross section, it is noted that the first and second chambers 740, 750 can include shapes other than those that are shown in FIG. 7, again depending upon the application of the implant 700, the patient, the insertion location of the implant 700, or other relevant factors.

An injection port 760, in an example, is disposed through the second endplate 720 and is in fluid communication with both the first chambers 740 and the second chambers 750. In a further example, the injection port 760 is divided into two channels 760A, 760B for fluid introduction, with a first channel 760A configured for introducing expansion medium into the second chambers 750 and a second channel 760B for introducing expansion medium into the first chambers 740. In the example of FIG. 7, the second channel 760B branches off to each of the first chambers 740 to allow for introduction of expansion medium into each of the first chambers 740, and the first channel 760A branches off to each of the second chambers 750 to allow for introduction of expansion medium into each of the second chambers 750. In another example, the injection port 760 is disposed through the first endplate.

In an example, once the implant 700 is determined to be optimally positioned with respect to the vertebral bodies, a pressured fluid, such as saline, or air is temporarily injected or pumped into the second chambers 750 by coupling a fill material introducer to the injection port 760. Introduction of the temporary pressurized fluid or air to the second chambers 750 via the injection port 760 forces the height of the implant 700 to expand and the first endplate and the second endplate 720 to be distracted from one another until they bear against and impart a desired amount of distraction between the remaining vertebral bodies, thereby providing provisional anterior column support, distraction, and/or restoration of proper spinal alignment. Once the desired implant height is achieved via the filling of the second chambers 750, in an example, a second fill material introducer is coupled to the injection port 760, and the first chambers 740 are filled with a permanent structural support material, such as PMMA, for instance, that is capable of being introduced in a fluid state and curing to a solid state to create a permanent, structural load bearing form. Once the permanent structural support material cures within the first chambers 740, the temporary pressurized fluid or air housed within the second chambers 750 is evacuated and a rigid, expanded implant 700 remains. In various examples, the permanent structural support material can incorporate bone graft, brachytherapy seeds, antibiotic, radiotherapeutic, or chemotherapeutic substances. The access channel is then sealed and the wound closed. In another example, the first chambers 740 can be filled with the temporary pressurized fluid or air and the second chambers 750 can be filled with the permanent structural support material.

In another example, FIG. 8 shows an expandable corpectomy device 800. It is noted that, in various examples, in addition to the features and properties described below, the implant 800 can include one or more features and/or one or more properties similar to those included with the implant examples discussed above. In an example, the implant 800 includes a first endplate (broken away in FIG. 8) configured to contact a first vertebral body and a second endplate 820 configured to contact a second vertebral body. In various examples, the first endplate and the second endplate 820 include teeth, serrations, ridges, or other anti-repulsion features to secure the first endplate and the second endplate 820 to the respective vertebral bodies.

In an example, the implant 800 includes an expansion bladder group 830. As shown in FIG. 8, the expansion bladder group 830 includes two first chambers 840 and two second chambers 850. In an example, the first and second chambers 840, 850 are arranged in a two-by-two array with each first chamber 840 disposed at diagonally opposite corners of the array and each second chamber 850 disposed at the other corners of the array. In other examples, other arrangements of the first and second chambers 840, 850 are contemplated. It is further contemplated that, in other examples, the implant 800 includes more or less than two first chambers 840 and more or less than two second chambers 850 depending upon the application of the implant 800, the patient, the insertion location of the implant 800, or other relevant factors. Although the first and second chambers 840, 850 are shown as substantially circular in cross section, it is noted that the first and second chambers 840, 850 can include shapes other than those that are shown in FIG. 8, again depending upon the application of the implant 800, the patient, the insertion location of the implant 800, or other relevant factors.

A first injection port 860A, in an example, is disposed through the second endplate 820 and is in fluid communication with the second chambers 850, and a second injection port 860B is disposed through the second endplate 820 and is in fluid communication with the first chambers 840. In a further example, the first injection port 860A is configured for introducing expansion medium into the second chambers 850, and the second injection port 860B is configured for introducing expansion medium into the first chambers 840. In the example of FIG. 8, the second injection port 860B branches off to each of the first chambers 840 to allow for introduction of expansion medium into each of the first chambers 840, and the first injection port 860A branches off to each of the second chambers 850 to allow for introduction of expansion medium into each of the second chambers 850. In another example, the first and second injection ports 860A, 860B are disposed through the first endplate.

In an example, once the implant 800 is determined to be optimally positioned with respect to the vertebral bodies, a pressured fluid, such as saline, or air is temporarily injected or pumped into the second chambers 850 by coupling a fill material introducer to the first injection port 860A. Introduction of the temporary pressurized fluid or air to the second chambers 850 via the first injection port 860A forces the height of the implant 800 to expand and the first endplate and the second endplate 820 to be distracted from one another until they bear against and impart a desired amount of distraction between the remaining vertebral bodies, thereby providing provisional anterior column support, distraction, and/or restoration of proper spinal alignment. Once the desired implant height is achieved via the filling of the second chambers 850, in an example, a second fill material introducer is coupled to the second injection port 860B, and the first chambers 840 are filled with a permanent structural support material, such as PMMA, for instance, that is capable of being introduced in a fluid state and curing to a solid state to create a permanent, structural load bearing form. Once the permanent structural support material cures within the first chambers 840, the temporary pressurized fluid or air housed within the second chambers 850 is evacuated and a rigid, expanded implant 800 remains. In various examples, the permanent structural support material can incorporate bone graft, brachytherapy seeds, antibiotic, radiotherapeutic, or chemotherapeutic substances. The access channel is then sealed and the wound closed. In another example, the first chambers 840 can be filled with the temporary pressurized fluid or air and the second chambers 850 can be filled with the permanent structural support material.

It will be appreciated by those skilled in the art that changes could be made to the examples described above without departing from the broad inventive concept thereof. It is understood, therefore, that this invention is not limited to the particular examples disclosed, but it is intended to cover modifications within the spirit and scope of the present invention as defined by the present description.

The above Detailed Description includes references to the accompanying drawings, which form a part of the Detailed Description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more features thereof) may be used in combination with each other. Other embodiments can be used, such as by one of ordinary skill in the art upon reviewing the above description. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

The Abstract is provided to allow the reader to quickly ascertain the nature of the technical disclosure. It is submitted with the understanding that it will not be used to interpret or limit the scope or meaning of the claims.

What is claimed is:

1. A method of vertebral body replacement, the method comprising:
  inserting an implantable device between a first vertebral body and a second vertebral body, the implantable device including a first endplate configured to contact the first vertebral body, a second endplate configured to contact the second vertebral body, and an expansion bladder disposed between and coupled to the first endplate and the second endplate, the expansion bladder including a first chamber and a second chamber, the first chamber and the second chamber being sealed from fluid communication with one another;

introducing a non-curable expansion fluid into the first chamber of the expansion bladder to separate the first and second endplates of the implantable device to achieve a final height of the implantable device;

introducing a curable structural support material into the second chamber of the expansion bladder to maintain the final height of the implantable device; and evacuating the non-curable expansion fluid from the first chamber after introducing the curable structural support material into the second chamber of the expansion bladder.

2. The method of claim 1, comprising introducing a substance into the first chamber after evacuation of the non-curable expansion fluid.

3. The method of claim 2, wherein introducing the substance into the first chamber includes introducing a therapeutic substance into the first chamber.

4. The method of claim 1, wherein introducing the expansion fluid includes separating the first and second endplates of the implantable device to cause the first endplate to contact the first vertebral body and to cause the second endplate to contact the second vertebral body.

5. A method of treatment of a spine including a damaged or diseased vertebral body disposed between first and second vertebral bodies, the method comprising:

providing an access channel to the spine;

removing the damaged or diseased vertebral body;

inserting, through the access channel, an implantable device between the first vertebral body and the second vertebral body, the implantable device including a first endplate configured to contact the first vertebral body, a second endplate configured to contact the second vertebral body, and an expansion bladder disposed between and coupled to the first endplate and the second endplate, the expansion bladder including a first chamber and a second chamber, the first chamber and the second chamber being sealed from fluid communication with one another;

introducing a non-curable expansion fluid into the first chamber of the expansion bladder to separate the first and second endplates of the implantable device to achieve a final height of the implantable device, wherein the first endplate is in contact with the first vertebral body and the second endplate is in contact with the second vertebral body;

introducing a curable structural support material into the second chamber of the non-curable expansion bladder to maintain the final height of the implantable device; and evacuating the expansion fluid from the first chamber after introducing the curable structural support material into the second chamber of the expansion bladder.

6. The method of claim 5, comprising introducing a substance into the first chamber after evacuation of the non-curable expansion fluid.

7. The method of claim 6, wherein introducing the substance into the first chamber includes introducing a therapeutic substance into the first chamber.

8. The method of claim 5, comprising sealing the access channel following insertion of the implantable device.

9. The method of claim 5, wherein inserting the implantable device includes inserting the implantable device with an initial height of the implantable device that is less than the final height.

\* \* \* \* \*

UNITED STATES PATENT AND TRADEMARK OFFICE
CERTIFICATE OF CORRECTION

PATENT NO.        : 8,632,592 B2           Page 1 of 1
APPLICATION NO.   : 13/141239
DATED             : January 21, 2014
INVENTOR(S)       : Ben Barrall It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 138 days.

Signed and Sealed this
Twenty-second Day of September, 2015

Michelle K. Lee
*Director of the United States Patent and Trademark Office*